(12) United States Patent
Yang et al.

(10) Patent No.: US 9,606,049 B1
(45) Date of Patent: Mar. 28, 2017

(54) GAS DETECTOR USING A GOLAY CELL

(71) Applicant: Honeywell International Inc., Morristown, NJ (US)

(72) Inventors: Wei Yang, Minnetonka, MN (US); Teresa M. Marta, White Bear Lake, MN (US); Martin Willett, Waterlooville (GB); Rodney R. Watts, Wimborne (GB)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 14/879,920

(22) Filed: Oct. 9, 2015

(51) Int. Cl.
| | | |
|---|---|---|
| *G01J 5/02* | (2006.01) | |
| *G01N 21/17* | (2006.01) | |
| *G01N 21/61* | (2006.01) | |
| *G01J 5/42* | (2006.01) | |
| *G01N 33/00* | (2006.01) | |

(52) U.S. Cl.
CPC .......... *G01N 21/1702* (2013.01); *G01J 5/02* (2013.01); *G01J 5/42* (2013.01); *G01N 21/61* (2013.01); *G01N 33/0027* (2013.01); *G01N 2021/1704* (2013.01); *G01N 2201/067* (2013.01); *G01N 2201/12* (2013.01)

(58) Field of Classification Search
CPC ..................................... G01J 5/02; G01J 5/42
USPC ...................... 250/343, 344, 346, 338.1, 332
See application file for complete search history.

(56) References Cited

U.S. PATENT DOCUMENTS

| | | | | |
|---|---|---|---|---|
| 4,891,629 A | * | 1/1990 | Gajjar ................... | G01N 25/18 340/632 |
| 7,045,784 B1 | * | 5/2006 | Ptasinski .................. | G01J 5/42 250/332 |
| 2006/0175547 A1 | * | 8/2006 | DiFoggio ................. | G01J 3/02 250/269.1 |

FOREIGN PATENT DOCUMENTS

JP    08184501    *  7/1996

OTHER PUBLICATIONS

Schjolber-Henriksen, et al., "Sensitive and Selective Photo Acoustic Gas Sensor Suitable for High Volume Manufacturing", IEEE Sensors 2006, EXCO, Daegu, Korea, Oct. 22-25, 2006, pp. 879-682.

* cited by examiner

*Primary Examiner* — David Porta
*Assistant Examiner* — Meenakshi Sahu
(74) *Attorney, Agent, or Firm* — Conley Rose, P.C.; Kristin Jordan Harkins

(57) ABSTRACT

Gas detector devices, systems, and methods using a Golay cell are described herein. One device includes a microphone having a front surface with an sound collecting aperture for receiving sound, a substrate, a gas cavity formed in the substrate such that the gas cavity is in gas communication with the sound collecting aperture and the front surface forms a side surface of the gas cavity, and a window abutting the substrate to form a side surface of the gas cavity.

20 Claims, 2 Drawing Sheets

GAS DETECTOR USING A GOLAY CELL

TECHNICAL FIELD

The present disclosure relates to devices, systems, and methods for creating and utilizing a gas detector using a Golay cell.

BACKGROUND

Gas detection based on a non-dispersive infrared (NDIR) technique, in particular those operating in the mid-wavelength IR (MWIR) (3000-8000 nm), generally lack efficient optical sources. And, in applications where a high signal to noise ratio is desired, optical power must be raised. This can result in high power consumption which can pose serious limitations on portable and/or wireless form factor operations, in some applications.

Alternatively, a more sensitive and lower noise detector can be used in some implementations to attain high performance without raising power consumption. However, commercially available MWIR detectors can be expensive, and some detectors require cooling which can add components to the system, among other possible issues, in such implementations.

DETAILED DESCRIPTION

Figure 1:
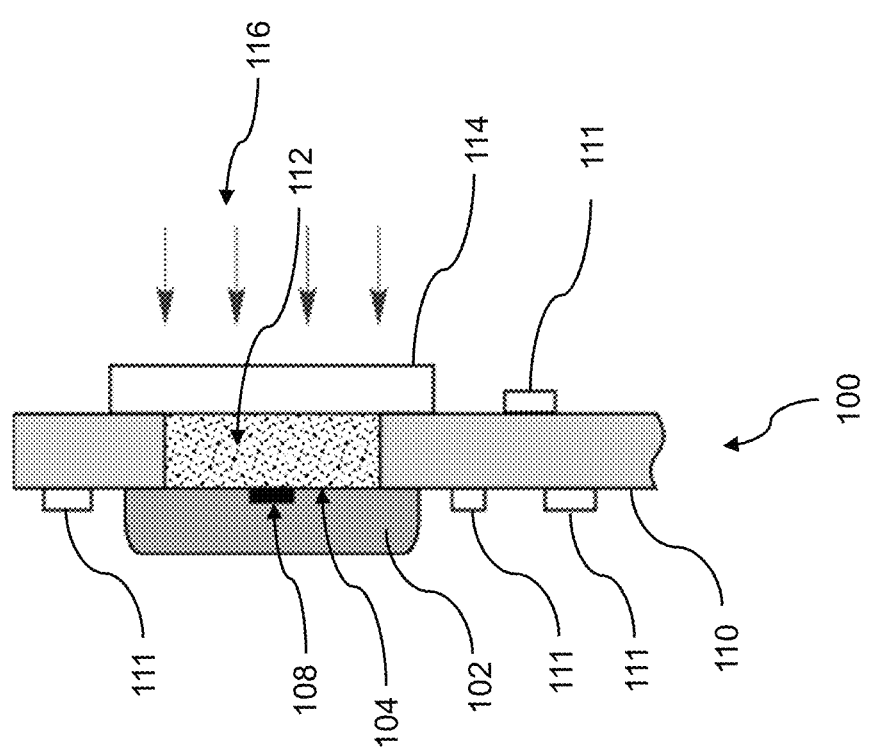
FIG. 1 illustrates a gas detector device in accordance with one or more embodiments of the present disclosure.

Gas detector devices, systems, and methods using a Golay cell are described herein. One such gas detector using a Golay cell includes a microphone having a front surface with a sound collecting aperture for receiving sound, a substrate, a gas cavity formed in the substrate such that the gas cavity is in gas communication with the sound collecting aperture and the front surface forms a side surface of the gas cavity, and a window abutting the substrate to form a side surface of the gas cavity.

The substrate that provides the structural basis for the gas cavity can be a printed circuit board (PCB) containing electronic components electrically interconnected with the microphone or other components of a device into which the gas detector is provided.

This disclosure describes creating and utilizing a gas detector using a Golay cell that can, for example, be used as a low cost light detector capable, for example, of detecting a very low level of MWIR radiation and its implementation in an NDIR detector. The detector embodiments of the present disclosure are based on the principle of a Golay cell which is used in infrared and terahertz radiation detections.

The Golay cell design of embodiments of the present disclosure can take advantage of the availability of low-cost, high sensitivity microelectromechanical system (MEMS) microphones proliferated by the mobile phone industry. The Golay cell in some embodiments, integrates the microphone with a gas cell of comparable volume, while using the gas or the microphone as an optical absorber. That is, the absorbing material can be the gas and/or the microphone.

In embodiments of the present disclosure, the pressure sensing element, (e.g., the diaphragm, in a conventional Golay cell) is part of the MEMS microphone and can provide sensitive detection of pressure fluctuation in a gas cavity due to absorption of electromagnetic radiation. As discussed above, this functionality would otherwise take a much more expensive and/or complex instrumentation to accomplish. In some embodiments of the present disclosure the microphone structure itself can be used as a heat sensor.

In the following detailed description, reference is made to the accompanying drawings that form a part hereof. The drawings show by way of illustration how one or more embodiments of the disclosure may be practiced.

These embodiments are described in sufficient detail to enable those of ordinary skill in the art to practice one or more embodiments of this disclosure. It is to be understood that other embodiments may be utilized and that process changes may be made without departing from the scope of the present disclosure.

As will be appreciated, elements shown in the various embodiments herein can be added, exchanged, combined, and/or eliminated so as to provide a number of additional embodiments of the present disclosure. The proportion and the relative scale of the elements provided in the figures are intended to illustrate the embodiments of the present disclosure, and should not be taken in a limiting sense.

Directional terms such as "horizontal" and "vertical" "above" and "below" are used with reference to the component orientation depicted in FIG. 1. These terms are used for example purposes only and are not intended to limit the scope of the appended claims.

The figures herein follow a numbering convention in which the first digit or digits correspond to the drawing figure number and the remaining digits identify an element or component in the drawing. Similar elements or components between different figures may be identified by the use of similar digits. For example, 100 may reference element "00" in FIG. 1, and a similar element may be reference as 200 in FIG. 2.

As used herein, "a" or "a number of" something can refer to one or more such things. For example, "a number of apertures" can refer to one or more apertures.

FIG. 1 illustrates a gas detector device in accordance with one or more embodiments of the present disclosure. In the embodiment illustrated in FIG. 1, the device 100 includes a microphone 102 having a front surface 104 and a sound collecting aperture 108, a gas cavity 112 formed in substrate 110 such that the gas cavity 112 is in gas communication with the aperture 108 and wherein the front surface forms a side surface of the gas cavity 112, and a 114 window abutting the substrate 110 to form a side surface of the gas cavity 112. In some embodiments, the substrate may have electronic components 111 mounted on one or both side of its surfaces. These components can be related to the functioning of the gas detector or can be components not related to the function of the gas detector, but located proximate to the gas detector.

In some embodiments, the window can include optical characteristics that change the characteristics of the light passing through the window. For example, the window can have a diffusing or collimating characteristic designed into the window. In some embodiments, the window could also be a lens or waveguide.

These optical characteristics can be accomplished based on the formation of the interior of the window, the formation and/or preparation (e.g., polishing) of one or more sides of the window, and/or through the use of coatings applied to the window on one or more sides. The window can also be coated with optical films to enhance or retard the transmission of light at certain wavelengths.

This may be beneficial in some embodiments to isolate or focus certain wavelengths for purposes of improving detection. For example, certain wavelengths that can be isolated or enhanced can be 3.3 and/or 3.4 microns for hydrocarbons, 4.3 microns for $CO_2$, or 9 microns for ammonia, among others.

In the embodiments of the present disclosure, the gas cavity (formed by other elements of the device, such as the one or more substrates, the window, and the microphone) can be a closed cell that does not allow interaction with the ambient surroundings. Accordingly, the gas within the closed cell can be selected to enhance the sensitivity for the presence of a particular gas or a particular set of gases.

In some embodiments, the substrate can be a printed circuit board (PCB) type material or other suitable material. Additionally, in some embodiments, the structure comprising the substrate can be of multiple layers rather than a single substrate layer, as shown in FIG. 1. In various embodiments, the microphone and/or the window can be attached to the substrate 110 such that the gas cavity 112 is hermetically sealed. Such embodiments allow for formation of a gas filled cavity which is fluidically connected to the microphone inlet port (i.e., aperture 108) but insulated from the ambient conditions.

When radiative power (e.g., light from a light source) 116 enters the gas cavity 112 through the window 114 and is absorbed by the gas and/or microphone surfaces, a small amount of heat can be generated. The heat causes a pressure rise which can be sensed by the microphone.

The fill gas in the cavity 112 can be selected to optimize the sensitivity and/or temperature range of the detector, based on parameters such as specific heat, thermal conductivity, permeability, triple point, and/or chemical stability, among other parameters that can be utilized based upon the operating conditions of the detector.

The fill gas can, for example, be nitrogen, hydrogen, argon, krypton, xenon, hydrocarbons, fluorocarbons, or a mixture of above gases, among other suitable gas types. In various embodiments, the pressure of the fill gas can be less or larger than the ambient pressure. For example, the fill gas pressure can range from 0.1 bar to 10 bar, in some embodiments.

An advantage of the detector is the isolation of the microphone from the ambient surroundings, thus eliminating interferences and instabilities due to environmental variables such as acoustic noise, pressure, density, moisture, chemicals, and particulates that are in the ambient surroundings around the device.

One benefit of using a PCB is to make electrical interconnects to the microphone (e.g., through surface mount soldering pads) thus the detector can be an integral part of a PCB and connected to other components on the same board.

In some applications, a user could have several of these devices (e.g., on the same substrate, such as a PCB) each having different gases in their respective gas cavity and they could be inserted into a larger system, to accomplish gas detection. Additionally, in some embodiments, a single device (e.g., the structure of FIG. 1 or a similar structure) could be used in a system (e.g., a structure like that of FIG. 2 or another suitable structure) and that device could be removed and replaced with another that could sense one or more other gases. In other embodiments, multiple devices could be used at the same time (e.g., either on the same substrate or on different substrates) to sense multiple gases or could have the same gas in the gas cavity and could provide redundancy, which could be beneficial as it would provide increased certainty that the gas detection was correct.

Figure 2:
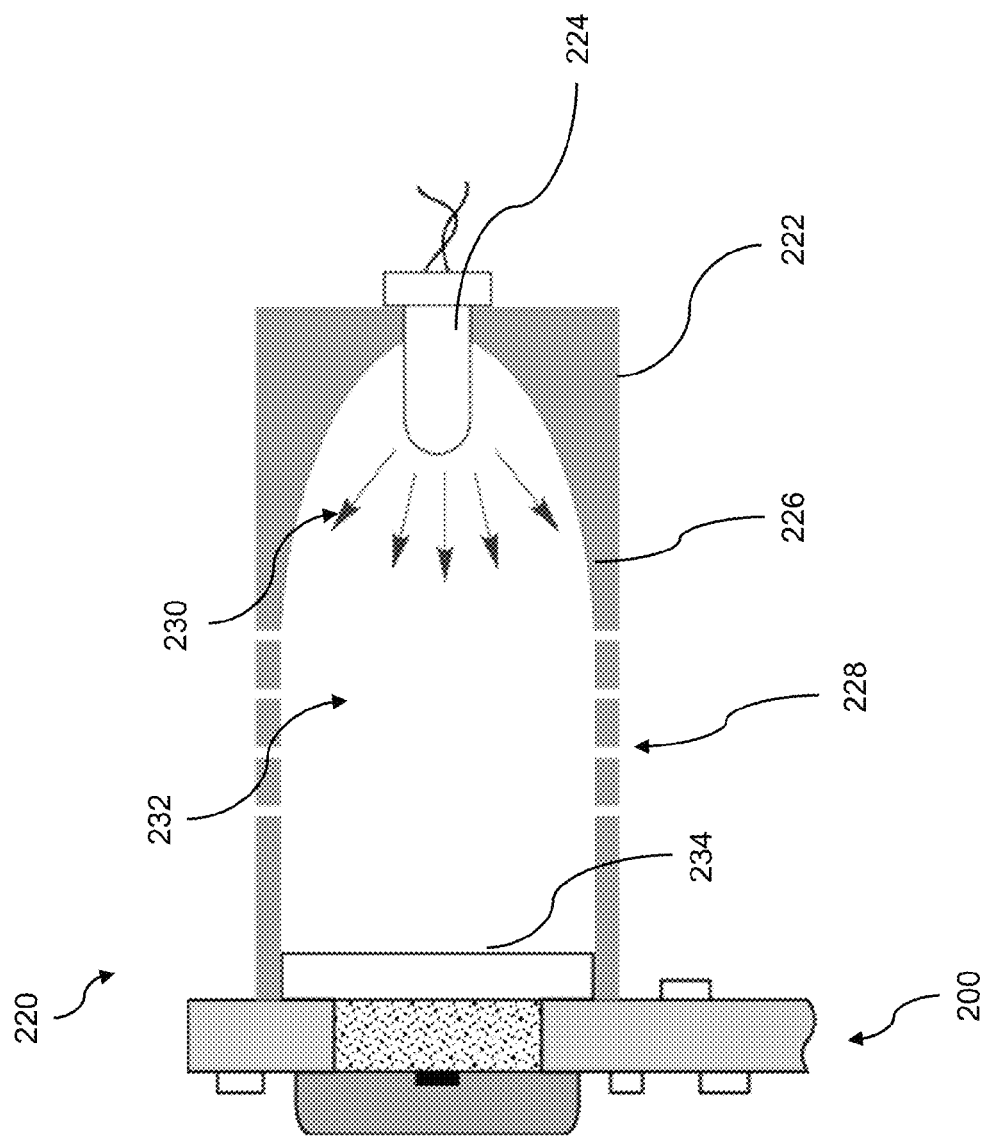
FIG. 2 illustrates a gas detector system in accordance with one or more embodiments of the present disclosure.

FIG. 2 illustrates a gas detector system in accordance with one or more embodiments of the present disclosure. FIG. 2 shows a gas detector design which can be compact and have low power consumption in many implementations.

In the embodiment of FIG. 2, the light wavelength detecting element 220 and an optical source 224 are face-to-face mounted on the opposite ends of an optical cavity 232, which can have a reflective internal surface finish 226 to facilitate maximum light entry into the detector 200.

The optical source can, for example, be one or more filament bulbs, microelectromechanical systems (MEMS) hotplates, light emitting diodes (LEDs), and/or lasers. Such components can all potentially be advantageously paired with detector embodiments described herein to provide a gas sensor with good performance.

The reflective surface does not need to be reflective to visible light in all applications, but rather, may be reflective to one or more wavelengths that will be used with respect to detecting the particular one or more gases within the gas cavity.

In some embodiments, the surface of the optical cavity may have a texture. The texture may provide a more homogeneous light pattern that is directed to the detector. Further, in some embodiments, the surface may be non-reflective.

At least part of the walls 222 of the optical cavity 232 are permeable to ambient gases via permeable material, holes (e.g., openings 228), or porous media (porous at least to the wavelengths of light that will be useful for detection), thus the presence of gases of interest in the ambient surroundings that absorb the radiation 230 could be detected by the detector when a reduction of received radiation 230 at specific wavelengths (e.g., for example, wavelengths such as 3.3 or 3.4 microns for hydrocarbons, 4.3 microns for $CO_2$, or 9 microns for ammonia, among others) is observed.

In order to be sensitive to specific gases, optical band-pass filters may be added as additional components in the optical path or a coating on the interior surface (nearer to the microphone) or the exterior surface 234 of the detector window. In some instances, even though the gas cavity has a particular gas therein, there may still be a need for filtering of ambient components that may have similar characteristics as the particular gas in the cavity.

In such situations, one or more filters, such as thin film, applied coatings, filters physically separate from the window, or other types of filters, could be placed in the path of the light from the light source to filter out such ambient noise (characteristics that may be mistaken for the particular gas in the cavity) associated with these ambient components. Such an implementation may also be done in applications having multiple gases within the cavity. Examples of ambient components that can be filtered can, for example, can include $CO_2$, water vapor, or condensed water, among others.

In some embodiments where modulated or, for example, alternating current (AC) is utilized, since the Golay cell is only sensitive to modulated optical intensity, the optical source must be modulated at a certain frequency, for example, a frequency in the 3 to 1000 Hz range. The gas detector of this configuration can be operated at extremely low power because the Golay cell is able to detect a very low level of radiative power thus the optical source can be energized at correspondingly low levels.

Embodiments of the present disclosure can be constructed as a micro-Golay detector device with an elongate size (width of widest side of the microphone) of the microphone component being 2-5 mm. With such embodiments, these devices could be used in small and/or portable applications and such devices may have a lower power consumption as opposed to devices on the magnitude of 10-20 mm width dimension. Another benefit of a micro-Golay device is the reduced ability of contaminants to get into the device.

The embodiments of the present disclosure can be used in a broad range of optical based gas detection including detection of flammable gases, toxic gases, and other environmentally relevant gases such as $CO_2$ and refrigerants. For example, a Golay cell detector device can be used as a standalone detector for electromagnetic radiation from deep UV to terahertz frequencies, among other implementations.

Although specific embodiments have been illustrated and described herein, those of ordinary skill in the art will appreciate that any arrangement calculated to achieve the same techniques can be substituted for the specific embodiments shown. This disclosure is intended to cover any and all adaptations or variations of various embodiments of the disclosure.

It is to be understood that the above description has been made in an illustrative fashion, and not a restrictive one. Combination of the above embodiments, and other embodiments not specifically described herein will be apparent to those of skill in the art upon reviewing the above description.

The scope of the various embodiments of the disclosure includes any other applications in which the above structures and methods are used. Therefore, the scope of various embodiments of the disclosure should be determined with reference to the appended claims, along with the full range of equivalents to which such claims are entitled.

In the foregoing Detailed Description, various features are grouped together in example embodiments illustrated in the figures for the purpose of streamlining the disclosure. This method of disclosure is not to be interpreted as reflecting an intention that the embodiments of the disclosure require more features than are expressly recited in each claim.

Rather, as the following claims reflect, inventive subject matter lies in less than all features of a single disclosed embodiment. Thus, the following claims are hereby incorporated into the Detailed Description, with each claim standing on its own as a separate embodiment.

What is claimed:

1. A gas detector device using a Golay cell, comprising:
    a microphone having a front surface with a sound collecting aperture for receiving sound;
    a substrate;
    a gas cavity formed in the substrate such that the gas cavity is in gas communication with the sound collecting aperture and the front surface forms a side surface of the gas cavity; and
    a window abutting the substrate to form a side surface of the gas cavity.

2. The device of claim 1, wherein the substrate includes a first substrate portion abutting the sound collecting surface and wherein the first substrate portion has an aperture formed through the first substrate portion with a first end of the aperture directed toward the sound collecting surface;
    a second substrate portion abutting the first substrate portion such that the second substrate portion forms side surfaces of a gas cavity and the first substrate portion forms a top surface of the gas cavity such that the gas cavity is in gas communication with the aperture.

3. The device of claim 1, wherein the window allows transmittance of light through the window.

4. The device of claim 1, wherein the window is opaque to all light that is not within a particular range of wavelengths.

5. The device of claim 1, wherein the gas cavity has ambient gas therein.

6. The device of claim 1, wherein gas cavity has only a particular gas therein.

7. The device of claim 1, wherein the gas cavity has only a particular set of gases therein.

8. The device of claim 1, wherein the cavity is sealed such that ambient gas cannot enter the cavity once it is sealed.

9. A gas detecting system using a Golay cell, comprising:
    a gas detector including:
        a microphone having front surface with a sound collecting aperture for receiving sound;
        a substrate abutting the front surface of the microphone;
        a gas cavity formed in the substrate such that the gas cavity is in gas communication with the aperture;
        a window abutting the substrate forming a side surface of the gas cavity;
    an optical generation chamber; and
    a light source to direct light toward the gas detector.

10. The system of claim 9, wherein the light source is within the optical generation chamber.

11. The system of claim 9, wherein the optical generation chamber is formed from at least one wall having a material that includes a gas permeable portion.

12. The system of claim 9, wherein the optical generation chamber is formed by an interior surface and at least a portion of the surface is reflective.

13. The system of claim 9, wherein the optical generation chamber is formed by an interior surface and the entire interior surface is reflective.

14. The system of claim 9, wherein the optical generation chamber is formed within a housing and wherein the housing includes one or more openings to allow ambient gas to pass into and out of the chamber.

15. The system of claim 9, wherein the light source is an infrared light source.

16. The system of claim 9, wherein the light source generates infrared light and the window is transparent to the infrared light generated thereby allowing the light to pass through the window.

17. A gas detector using a Golay cell, comprising:
    a microphone having a sound collecting aperture for receiving sound;
    a substrate having a first surface abutting the sound collecting surface and a second surface and a gas cavity formed between the first surface and the second surface of the substrate and wherein the gas cavity is in gas communication with the sound collecting aperture; and
    a window abutting the second surface of the substrate to seal the gas cavity.

18. The detector of claim 17, wherein the microphone and substrate are hermetically sealed together.

19. The detector of claim 17, wherein the substrate includes multiple layers.

20. The detector of claim 19, wherein the layers of the substrate are hermetically sealed together.

* * * * *